Figure 2:
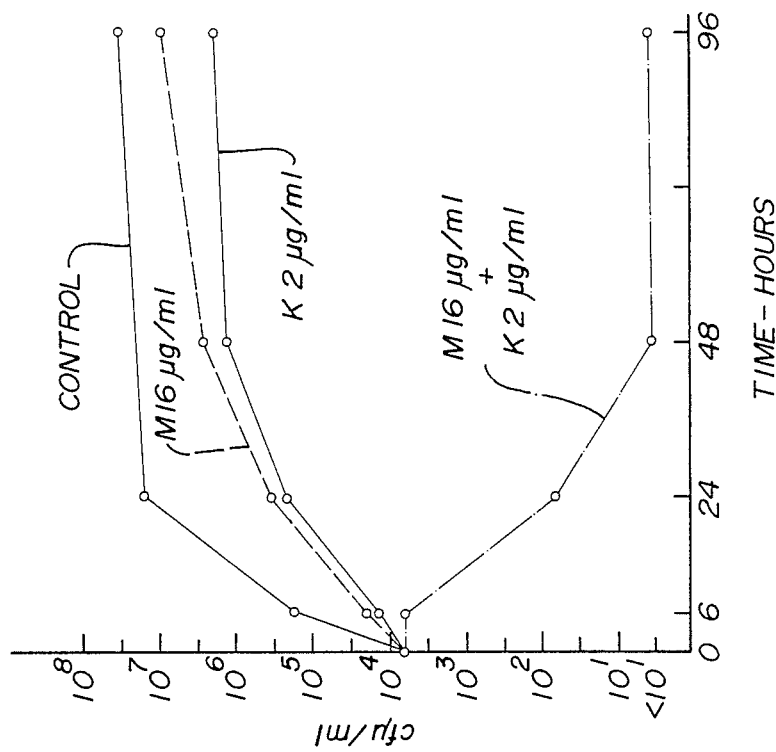

United States Patent [19]

Gadebusch et al.

[11] Patent Number: 4,871,741

[45] Date of Patent: Oct. 3, 1989

[54] METHOD OF CONTROLLING MYCOTIC INFECTIONS AND COMPOSITIONS THEREFOR

[75] Inventors: Hans H. Gadebusch, Yardley, Pa.; Mary E. Valiant, Plainfield, N.J.

[73] Assignee: Merck & Co., Inc., Rahway, N.J.

[21] Appl. No.: 9,866

[22] Filed: Feb. 2, 1987

[51] Int. Cl.[4] ................... A61K 31/495; A61K 31/35
[52] U.S. Cl. .................................. 514/255; 514/460
[58] Field of Search ............... 514/250, 460, 255, 548, 514/253, 397, 399

[56] References Cited

U.S. PATENT DOCUMENTS 4,319,039  3/1982  Albers-Schonberg .............. 560/256
4,342,767  8/1982  Albers-Schonberg et al. ..... 514/548

OTHER PUBLICATIONS

R. A. Fromtling, Drugs of Today, 20, 325–349, (1984).
I. J. Sud et al., Antimicrobial Agents and Chemotherapy, 28, 532–534, (1985).

*Primary Examiner*—Douglas W. Robinson
*Assistant Examiner*—Raymond J. Henley, III
*Attorney, Agent, or Firm*—Alice O. Robertson; Michael C. Sudol

[57] ABSTRACT

Certain fungistats when employed in combination have been found to exhibit synergistic antifungal properties and further exhibit fungicidal properties.

9 Claims, 1 Drawing Sheet

METHOD OF CONTROLLING MYCOTIC INFECTIONS AND COMPOSITIONS THEREFOR

BACKGROUND OF THE INVENTION

Fungal diseases or mycoses may be superficial, affecting primarily skin, hair and mucous membrane, or may be deep or systemic, affecting lungs and other internal organs. The superficial mycotic infections which are caused by organisms referred to as dermatophytes are generally considered more annoying than serious. The deep or systemic mycotic infections which are caused generally by a different organisms are quite serious, frequently resulting in death.

Antifungal agents considered with specific reference to deep or systemic fungal infections caused by organisms such as Candida species, *Cryptococcus neoformans*, *Histoplasma capsulatum* and the like, are found for the most part to be fungistatic, i.e., merely inhibit the growth of the fungal organism without effecting a kill. A few fungicidal agents are known. Amphotericin B and other polyenes are known to damage membranes that contain ergosterol and therefore are effectively fungicidal. However, their use is normally precluded because of a number of severe side effects. Other possibly fungicidal drugs have side effects or may be limited by the scope of their spectrum, e.g. 5-fluorocytosine. 5-Fluorocytosine is further limited by the ease with which an organism develops resistance to it. In the search for antifungal drugs, for treating systemic infections, it is desirable to find a drug or a combination of drugs which is effective at low concentration levels thereby minimizing side effects. It is particularly desirable to find a drug or a combination of drugs in which the drug is fungicidal.

STATEMENT OF THE INVENTION

The present invention concerns an improved method for the treatment of deep or systemic mycotic infections made possible by the discovery that when certain fungistatic agents known to be inhibitors in fungal sterol synthesis are employed in combination, a synergistic antifungal combination is obtained. It has further been found that the combination not only inhibits the growth of fungi to an extent much greater than that which would result from an additive effect of the component but that such amounts are able to cause irreversible damage to the fungi resulting in a killing or cidal effect on the fungi. The invention also concerns compositions which are suitable for use in the treatment of systemic mycotic infections.

DESCRIPTION OF THE INVENTION

The fungistats which in combination have been found to produce this unexpected synergistic and fungicidal effect have been found to belong to a class of compounds which are known to be inhibitors of 14α-methyldemethylase and inhibitors of HmG-CoA-reductase. By using a combination of compounds from compounds having these properties there is provided a method for treating mycotic infections.

The process of the present invention comprises treating subjects with mycotic infections by directing to the site where control is desired of a therapeutically effective antifungal amount of a composition comprising (1) a compound which has a 14α-methylase inhibitor property and (2) a compound which has a HmG-CoA-reductase inhibitor property. By "directing to the site where control is desired" is meant that the application may be made at a site remote from that of the infection such as would be the case with oral or parenteral administration. The agents may be administered simultaneously or sequentially and either agent may be administered first. They may be administered with or without a pharmaceutically acceptable carrier in the amounts hereinafter set forth. By the administration of the amounts of the agents as hereinafter set forth, a synergistic interaction and further a fungicidal effect of the drugs is achieved which is wholly unexpected. The preferred method of administration may vary with the site where control is desired. One preferred method of administration is by the use of pharmaceutical compositions in unit dosage form as described below which provides a convenient simultaneous administration method.

The compounds which have 14α-methyldemethylase inhibitor activity which are essential as one component of the antifungal compositions to be employed in treating human mycotic infections preferably are azoles, especially imidazoles and triazoles. Many of these compounds are in use clinically as fungistats or are being developed for such purpose. The generic drug names for those compounds already developed or being developed have the suffix "conazole". In subsequent discussions, the compounds will sometimes be referred to as "conazole compounds", even though some may not have a generic name. The foremost compound is ketoconazole which is cis-l-acetyl-4-[4-[[2-(2,4-dichlorophenyl)-2(1H-imidazole-1-ylmethyl)-1,3-dioxolan-4-yl]methoxy]phenyl]piperazine. Other fungistatic conazole compounds which are 14α-methyldemethylase inhibitors and which are either in clinical use or in development include miconazole, 1-[2,4-dichloro-β-(2,4-dichlorobenzyloxy)phenethyl]imidazole as nitrate; econazole, 1-[2-(2,4-dichlorophenyl)-2-(4-chlorobenzyloxy)ethyl]imidazole; isoconazole, 1-[2,4-dichloro-β-(2,6-dichlorobenzyloxy)phenethyl]imidazole as nitrate; terconazole, cis-1,4,2-(2,4-dichlorophenyl)-2-(1-ylmethyl)-1,3-dioxolan-4-ylmethoxyphenyl-4-(methylethyl)-piperazine; tioconazole, 1-[2-[(2-chloro-3-thienyl)methoxy]-2-(2,4-dichlorophenyl)ethyl]-1H-imidazole; bifonazole, 1-[(4-biphenyl)phenylmethyl]-1H-imidazole. Still other azoles include ICI-153066 (ICI Pharmaceutical Division), [(R,S)-1-(2,4-dichlorophenyl)-1-(4-fluorophenyl)-2-(1,2,4-triazol-l-yl)ethanol]; Bay-n-7133 (Bayer AG, West Germany), 1-(4-chlorophenoxy)-3,3'-dimethyl-2-(1,2,4-triazol-l-yl)methylbutan-2-ol; (E)-1-(5-chlorothien-2-yl)-2-(1H-imidazole-l-yl) ethanone-2,6-dichlorophenylhydrazone hydrochloride; SM-4470 (Sumitomo Chemical Co., Ltd.), (R)-3-(n-butylthio)-2-(2,4-dichlorophenyl)-1-(imidazole-l-yl)-2- propanol hydrochloride; oriconazole or itra-conazole, (+)-cis-4-[4-[4-[[2-(2,4-dichlorophenyl)-2-(1H-1,2,4-triazol-l-ylmethyl)-1,3-dioxolan-4-yl]methoxy]phenyl]-1-piperazinyl]phenyl]-2,4-dihydro-2-(1-methylopropyl)-3H-1,2,4-triazole-3-one; fenticonazole, α-(2,4-dichlorophenyl)-β,N-imidazolylethyl-4-phenyl-thiobenzylether nitrate; oxiconazole, (Z)-[(2,4-dichloro-2-imidazole-l-yl)acetophenone]-O-(2,4-di-chlorobenzyl)oxime; omoconazole (E)-1-[2,4-chloro-β-[2-(p-chlorophenoxy)ethoxy]-α-methylstyryl-]imidazole; aliconazole. Still other imidazole antifungal compounds which may be employed include 1-methyl-4-[3-(2-methyl-5-nitro-1H-imidazole-l-yl)propyl]piperazine, 5-nitro-(1-methylimidazolyl-t-butyl)(2-hydroxy-5-methoxyphenyl)carbinol, Z-1-[2-(2,4-dichlorophenyl)-3- methyl-l-pentenyl]-1H-imidazole hydrochloride, cis-3-(2-chloro-3-thienylmethyloxy)-2,3-dihydro-5-fluoro-2-(1-imidazoylmethyl)benzo[b]thiophene.

The compounds may have a basic nitrogen and therefore may be present as an acid addition salt. Reference to conazole compounds is intended to embrace both forms.

The HmG-CoA-reductase inhibitors ("reductase inhibitor") which are useful in the present invention include salts of an acid commonly known as mevinolinic acid. The compound has a chemical name 7-[1,2,6,7,8,8a(R)-hexahydro-2(S),6(R)-dimethyl-8(S)-(2(S)-methyl-butyryloxy)naphthyl-l(S)]-3(R),5(R)-dihydroxyheptanoic acid and may be represented by the formula

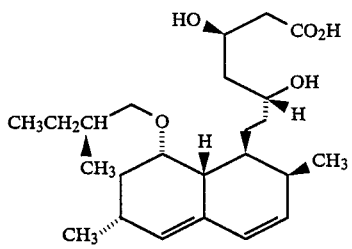

Another name by which it has been identified is 1,2,6,7,8,8a-hexahydro-β,β-δ,β-dihydroxy-2β,6α-dimethyl-8α-(2-methyl-l-oxobutoxy)-1β-naphthalenehep-tanoic acid. Suitable salts are ammonium, sodium, potassium and other water soluble salts. The salts of melvinolinic acid also may be referred to as to the respective mevinolinates, e.g., ammonium mevinolinate. The compounds may be obtained by isolation from a fermentation medium resulting after cultivation of a microorganism belonging to the genus Aspergillus as described in U.S. Pat. No. 4,342,767 and U.S. Pat. No. 4,319,039. The compounds useful in the practice of the present invention are hereinafter generically referred to as "mevinolinic acid compounds". It is essential that mevinolinic acid be employed in the form of its salt because of the tendency for mevinolinic acid as free acid to lactonize to mevinolin. (The latter is now known by its USAN name "lovastatin.") The lactone is not useful in the practice of the present invention.

Many of the conazole compounds are established antifungal compounds. With the greater efficacy and further, fungicidal properties made possible by its use in combination with mevinolinic acid compound or other reductase inhibitors, their potential in control of mycotic infections is greatly enhanced. Ketoconazole is one of the preferred antifungal compounds for its broad spectrum and substantial absence of side effects. The combination of ketoconazole and a mevinolinic acid compound represents a preferred embodiment of the present invention.

The synergistic antifungal and fungicidal combinations of the present invention are effective in the treatment of mycotic infections caused by such fungal organisms as Candida species, for example, C. albicans, C. tropicalis, C. stellatoidea; and Aspergillius species, such as A. fumigatus and A. flavus.

The efficacy of the combination of the present invention in producing a synergistic antifungal as well as a fungicidal effect may be seen in the in vitro interaction studies for the determination of activity and determination of viable cells. Synergistic antifungal properties have been demonstrated with ketoconazole and mevinolinic acid compound in tests against representative fungal organisms known to be the causative agent of mycotic infections, such as Candida albicans, several species of Aspergillus, and others. Representative synergistic antifungal and fungicidal properties of combinations may be demonstrated against Candida albicans, with ketoconazole and mevinolinic acid ammonium salt (ammonium mevinolinate).

SYNERGISTIC EFFECT MEVINOLINIC ACID COMPOUND AND KETOCONAZOLE

EXAMPLE A

Ammonium mevinolinate and ketoconazole were dissolved in dimethylformamide (DMF) and diluted with sterile distilled water to obtain a concentration of drug of 1.28 milligrams/millimeter in 10 percent DMF. Subsequent serial twofold dilutions were made with water.

Drug-agar plates were then prepared by adding molten Kimmig's agar (E. Merck, Darmstadt, W. Germany) supplemented with 0.5 percent glycerol to aliquots of the diluted samples. Nine parts of agar were employed for each part of solution containing drug or a mixture of drugs. Where a mixture of drugs was to be tested, the solutions containing the drugs were mixed immediately prior to the addition of agar.

Yeast fungal cultures which had been maintained on Sabouraud's dextrose agar were transferred to fresh medium and incubated at 35° C. (with shaking at 250 rpm) for 24 hours. They were suspended in 0.85 percent saline and adjusted to a turbidity reading of +2 using a Wickerham card. Plate counts of representative cultures performed previously indicate that this reading is equal to final concentrations of fungi of from about $3 \times 10^5$ to approximately $3 \times 10^6$ cfu/ml (colony forming units per milliliter). The Aspergillus strains were maintained on potato dextrose agar and the spore suspensions were prepared by the addition of saline to the slants followed by vigorous shaking with sterile glass beads.

The drug-agar plates were inoculated with fungal cultures using a Denley Multipoint Inoculator which delivers approximately 0.001 milliliter to the agar surface resulting in inocula of $3 \times 10^2$ to $3 \times 10^3$ cfu/ml. The plates were then incubated at 28° C. for 48 hours, read, and the minimum inhibitory concentrations (MIC) recorded. MIC was taken as the lowest concentration showing no growth or less than 3 cfu/spot.

Determination of the existance of synergism was made following procedure in "Antibiotics in Laboratory Medicine", by Victor Lorian, William and Wilkens, 1980, pp. 300–304. Drug combinations were considered to be synergistic when the "FIC index" (fractional inhibitory concentration index) was found to be ≦0.5. The fractional inhibitory concentration (FIC) for each drug was determined by dividing the minimum inhibitory concentration (MIC) of the drug when in combination by the MIC of the drug when tested alone. The FIC index is the summation of the two values. An FIC index of >0.5 and <2.0 is considered to indicate an additive effect and ≧2.0 to indicate an antagonistic effect.

The results of combinations which showed synergistic effect are seen in Table I.

TABLE I

| Fungal Organism | Strain Number | Minimum Inhibitory Concentration ug/ml | | FIC Index |
|---|---|---|---|---|
| | | Ammonium Mevinolinate. | Ketoconazole | |
| *Aspergillus fumigatus* | MF 4839* | 512.0 | 8.0 | 0.25 |
| *A. flavus* | MF 383 | 512.0 | 4.0 | 0.31 |
| *Candida albicans* | MY 992 | >512.0 | 8.0 | 0.28 |
| *C. tropicalis* | MY 1011 | 512.0 | 32.0 | 0.38 |
| *C. stellatoidea* | MY 1017 | 128.0 | 0.125 | 0.50 |

*Internal identification of strain of organism

EXAMPLE B

In operations carried out in a manner similar to that described in Example A, ammonium mevinolinate and ketoconazole were tested against 21 additional strains of *Candida albicans* in an agar dilution assay. Each compound was tested alone and in combination in a checkerboard square arrangement.

Ammonium mevinolinate was dissolved in water at a concentration of 5.12 mg/ml. Ketoconazole was dissolved in DMF and diluted with water to a concentration of 1.28 mg/ml in 10% diluent. Subsequent serial twofold dilutions were prepared in water.

Drug agar plates were prepared as previously described.

The yeast cultures, which had been maintained on Sabouraud's dextrose agar, were transferred to yeast maltose (YM) broth and incubated at 35° C. with shaking (250 rpm) for 24 hours. Appropriate dilutions were made with 0.85% saline to yield final concentrations of approximately $1 \times 10^6$ cfu/ml.

Drug-agar plates were (Kimmig's agar) inoculated with cultures using a Denley Multipoint Inoculator (Denley, Sussex, England) delivering approximately 0.001 milliliter to the agar surface resulting in inocula of $1 \times 10^3$. The plates were incubated at 28° C. for 48 hours, and the minimum inhibitory concentration (MIC) was recorded at the lowest concentration showing no growth or less than 3 cfu/spot. Against these cultures, there were many instances in which the mevinolinic acid compound reduced growth somewhat at levels below the MIC. These were also recorded and used for calculating the FIC for this compound.

The results of the combinations are seen in Table II.

TABLE II

| Fungal Organism | Strain Number | MINIMUM INHIBITORY CONCENTRATION (mg/ml) | | FIC Index |
|---|---|---|---|---|
| | | Ammonium Mevinolinate* | Ketoconazole | |
| *Candida albicans* | MY 1094 | 128–512 | 0.5 | 1.0 |
| *C. albicans* | MY 1115 | 32–128 | 16.0 | 0.13–0.31 (3)** |
| *C. albicans* | 7.251 | 16–64 | 0.25 | 0.31–0.5 (3) |
| *C. albicans* | 7.252 | 32–128 | 0.125 | 0.75 |
| *C. albicans* | 7.253 | 16–64 | 0.06 | 1.25 |
| *C. albicans* | 7.254 | 8–32 | 0.125 | 0.25–0.38 (2) |
| *C. albicans* | 7.255 | 32–128 | 16.0 | 0.06–0.25 (3) |
| *C. albicans* | 7.257 | 16–128 | 16.0 | 0.07–0.25 (3) |
| *C. albicans* | 7.258 | 16–128 | 16.0 | 0.07–0.25 (3) |
| *C. albicans* | 7.259 | 16–128 | 0.125 | 0.25–0.5 (3) |
| *C. albicans* | 7.260 | 8–64 | 0.25 | 0.19–0.31 (2) |
| *C. albicans* | 7.261 | 32–128 | 0.25 | 0.16–0.38 (4) |
| *C. albicans* | 7.262 | 32–256 | 16.0 | 0.04–0.25 (4) |
| *C. albicans* | 7.263 | 16–64 | 0.06 | 1.0 |
| *C. albicans* | 7.264 | 256 | 0.5 | 1.0 |
| *C. albicans* | 7.267 | 32–64 | 16.0 | 0.13–0.25 (3) |
| *C. albicans* | 7.268 | 16–128 | 0.25 | 0.31–0.38 (3) |
| *C. albicans* | 7.269 | 256–512 | 16.0 | 0.05–0.27 (6) |
| *C. albicans* | 7.271 | 32–128 | 16.0 | 0.25–0.38 (3) |
| *C. albicans* | 7.275 | 8–32 | 0.125 | 0.75 |
| *C. albicans* | 7.276 | 16–64 | 16.0 | 0.25–0.38 (2) |

*The higher figure is absolute MIC; the lower figure is reduced growth and used for calculating FIC.
**Figure in parenthesis is number of combination sets where synergy was observed.

FUNGICIDAL EFFECT MEVINOLINIC ACID COMPOUND AND KETOCONAZOLE

EXAMPLE C

Ammonium mevinolinate and ketoconazole were tested alone and in combination against *Candida albicans* 7.262 using a broth dilution method and plating procedures to determine the number of colony forming units at appropriate intervals.

Drug solutions were prepared as described in Example B, and tubes containing one part of drug or mixtures of drugs were inoculated with nine parts of broth (Kimmig's medium) seeded with culture. The culture was restored from an agar slant and grown in broth as described previously. The 24 hour culture (ca $10^8$ cfu/ml) was diluted 1:100 with 0.85% saline and a subsequent 1:100 dilution was made using Kimmig's medium to obtain approximately $10^4$ cfu/ml in the drug-culture tubes.

The inoculated tubes were incubated at 35° C. without shaking and aliquots were removed at 6, 24, 48, and 96 hours for dilution in saline and plating in Sabouraud's dextrose agar. The plates were incubated at 35° C. for at least 48 hours before the colonies were counted, and the number of cfu/ml in the undiluted drug-culture tubes was calculated from the counts obtained.

Figure 1:
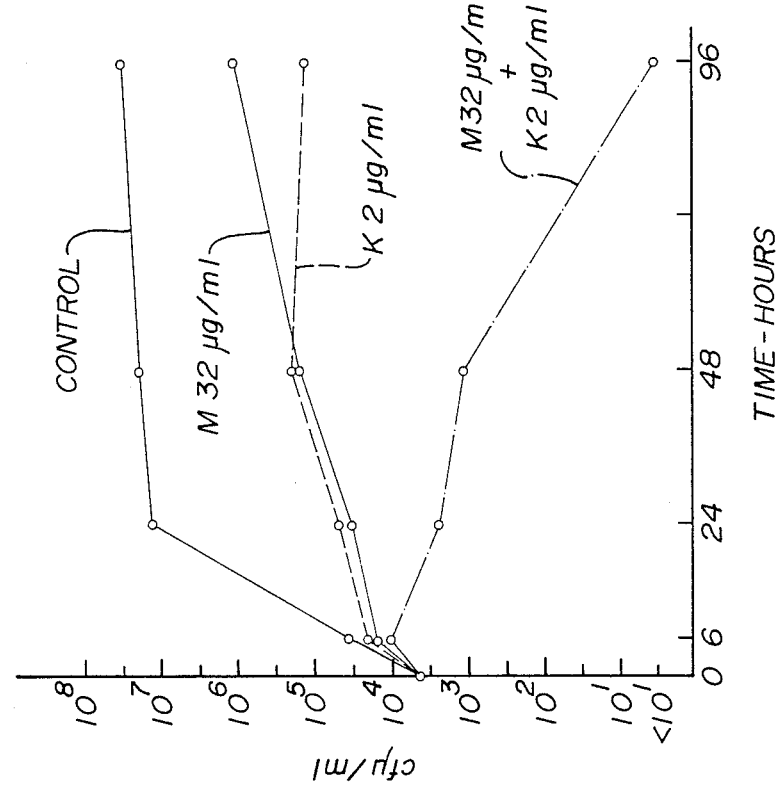

The results are seen in Table III and in FIG. 1.

TABLE III

| | ug/ml | Stationary Test Inoculum = $6.0 \times 10^3$ cfu/ml* | | | | |
|---|---|---|---|---|---|---|
| | | 0 hrs | 6 hrs | 24 hrs | 48 hrs | 96 hrs |
| Control | 0** | $6.0 \times 10^3$ | $5.6 \times 10^4$ | $1.6 \times 10^7$ | $2.7 \times 10^7$ | $5.0 \times 10^7$ |
| Ammonium | 16 | $6.0 \times 10^3$ | $3.8 \times 10^4$ | $4.8 \times 10^5$ | $1.1 \times 10^6$ | $3.2 \times 10^6$ |
| Mevinolinate (M) | 32 | $6.0 \times 10^3$ | $2.2 \times 10^4$ | $5.0 \times 10^4$ | $1.8 \times 10^5$ | $1.0 \times 10^6$ |
| | 64 | $6.0 \times 10^3$ | $2.1 \times 10^4$ | $1.4 \times 10^4$ | $1.0 \times 10^4$ | $8.9 \times 10^3$ |
| | 256 | $6.0 \times 10^3$ | $8.0 \times 10^3$ | $1.2 \times 10^2$ | $<1.0 \times 10^1$# | $<1.0 \times 10^1$# |
| Ketoconazole (K) | 2 | $6.0 \times 10^3$ | $3.1 \times 10^4$ | $7.3 \times 10^4$ | $1.9 \times 10^5$ | $1.3 \times 10^5$ |
| | 8 | $6.0 \times 10^3$ | $2.6 \times 10^4$ | $5.9 \times 10^4$ | $7.6 \times 10^4$ | $9.0 \times 10^4$ |
| | 32 | $6.0 \times 10^3$ | $2.4 \times 10^4$ | $3.2 \times 10^4$ | $4.5 \times 10^4$ | $7.9 \times 10^4$ |
| | 128 | $6.0 \times 10^3$ | $1.8 \times 10^4$ | $3.7 \times 10^4$ | $6.4 \times 10^4$ | $4.9 \times 10^4$ |
| (M) 16 + (K) | 2 | $6.0 \times 10^3$ | $1.9 \times 10^4$ | $1.0 \times 10^4$ | $9.0 \times 10^3$ | $1.2 \times 10^3$ |
| (M) 16 + (K) | 8 | $6.0 \times 10^3$ | $2.0 \times 10^4$ | $8.5 \times 10^3$ | $1.2 \times 10^3$ | $6.0 \times 10^1$ |
| (M) 16 + (K) | 32 | $6.0 \times 10^3$ | $1.5 \times 10^4$ | $8.6 \times 10^3$ | $1.5 \times 10^3$ | $<1.0 \times 10^1$# |
| (M) 32 + (K) | 2 | $6.0 \times 10^3$ | $1.6 \times 10^4$ | $3.9 \times 10^3$ | $1.4 \times 10^3$ | $<1.0 \times 10^1$# |
| (M) 32 + (K) | 8 | $6.0 \times 10^3$ | $1.6 \times 10^4$ | $1.8 \times 10^3$ | $<1.0 \times 10^1$# | $<1.0 \times 10^1$# |
| (M) 32 + (K) | 32 | $6.0 \times 10^3$ | $1.5 \times 10^4$ | $1.0 \times 10^3$ | $<1.0 \times 10^1$# | $<1.0 \times 10^1$# |
| (M) 64 + (K) | 2 | $6.0 \times 10^3$ | $1.4 \times 10^4$ | $2.9 \times 10^2$ | $<1.0 \times 10^1$# | $<1.0 \times 10^1$# |
| (M) 64 + (K) | 8 | $6.0 \times 10^3$ | $1.4 \times 10^4$ | $<1.0 \times 10^1$# | $<1.0 \times 10^1$# | $<1.0 \times 10^1$# |
| (M) 64 + (K) | 32 | $6.0 \times 10^3$ | $1.1 \times 10^4$ | $<1.0 \times 10^1$# | $<1.0 \times 10^1$# | $<1.0 \times 10^1$# |

*Determined after dilution with saline and plating on Sabouraud's dextrose agar.
**Control tube and all drug-culture tubes contained a final concentration of 1% DMF.
$<1.0 \times 10^1$ = lower limit of the assay.

EXAMPLE D

Operations were carried out in a manner similar to that described in EXAMPLE III except that the organism employed was *Candida albicans* MY 1055.

The results are seen in Table IV and in FIG. 2.

TABLE IV

| | ug/ml | Stationary Test Inoculum = $7.8 \times 10^3$ cfu/ml* | | | | |
|---|---|---|---|---|---|---|
| | | 0 hrs | 6 hrs | 24 hrs | 48 hrs | 96 hrs |
| Control | 0** | $7.8 \times 10^3$ | $1.9 \times 10^5$ | $2.2 \times 10^7$ | $3.3 \times 10^7$ | $4.6 \times 10^7$ |
| Ammonium | 16 | $7.8 \times 10^3$ | $2.9 \times 10^4$ | $4.8 \times 10^5$ | $4.3 \times 10^6$ | $9.7 \times 10^6$ |
| Mevinolinate (M) | 32 | $7.8 \times 10^3$ | $1.5 \times 10^4$ | $2.9 \times 10^4$ | $6.8 \times 10^5$ | $7.9 \times 10^5$ |
| | 64 | $7.8 \times 10^3$ | $1.5 \times 10^4$ | $3.3 \times 10^3$ | $2.1 \times 10^5$ | $3.8 \times 10^5$ |
| | 256 | $7.8 \times 10^3$ | $7.1 \times 10^3$ | $8.0 \times 10^1$ | $7.5 \times 10^2$ | $4.2 \times 10^3$ |
| Ketoconazole (K) | 2 | $7.8 \times 10^3$ | $3.2 \times 10^4$ | $4.0 \times 10^5$ | $1.4 \times 10^6$ | $2.2 \times 10^6$ |
| | 8 | $7.8 \times 10^3$ | $2.3 \times 10^4$ | $7.3 \times 10^4$ | $1.5 \times 10^5$ | $2.3 \times 10^5$ |
| | 32 | $7.8 \times 10^3$ | $3.1 \times 10^4$ | $3.8 \times 10^4$ | $3.1 \times 10^4$ | $1.2 \times 10^4$ |
| | 128 | $7.8 \times 10^3$ | $2.4 \times 10^4$ | $3.2 \times 10^4$ | $3.5 \times 10^4$ | $1.4 \times 10^4$ |
| (M) 16 + (K) | 2 | $7.8 \times 10^3$ | $8.1 \times 10^3$ | $8.0 \times 10^1$ | $<1.0 \times 10^1$# | $1.0 \times 10^1$# |
| (M) 16 + (K) | 8 | $7.8 \times 10^3$ | $1.0 \times 10^4$ | $5.0 \times 10^1$ | $<1.0 \times 10^1$# | $1.0 \times 10^1$# |
| (M) 16 + (K) | 32 | $7.8 \times 10^3$ | $1.1 \times 10^4$ | $9.0 \times 10^1$ | $<1.0 \times 10^1$# | $1.0 \times 10^1$# |
| (M) 32 + (K) | 2 | $7.8 \times 10^3$ | | CONTAMINATED TUBE | | |
| (M) 32 + (K) | 8 | $7.8 \times 10^3$ | $7.8 \times 10^3$ | $<1.0 \times 10^1$# | $<1.0 \times 10^1$# | $1.0 \times 10^1$# |
| (M) 32 + (K) | 32 | $7.8 \times 10^3$ | $8.3 \times 10^3$ | $<1.0 \times 10^1$# | $<1.0 \times 10^1$# | $1.0 \times 10^1$# |
| (M) 64 + (K) | 2 | $7.8 \times 10^3$ | $7.2 \times 10^3$ | $<1.0 \times 10^1$# | $<1.0 \times 10^1$# | $1.0 \times 10^1$# |
| (M) 64 + (K) | 8 | $7.8 \times 10^3$ | $7.4 \times 10^3$ | $<1.0 \times 10^1$# | $<1.0 \times 10^1$# | $1.0 \times 10^1$# |
| (M) 64 + (K) | 32 | $7.8 \times 10^3$ | $5.2 \times 10^3$ | $<1.0 \times 20^1$# | $<1.0 \times 10^1$# | $1.0 \times 10^1$# |

*Determined after dilution with saline and plating on Sabouraud's dextrose agar.
**Control tube and all drug-culture tubes contained a final concentration of 1% DMF.
$<1.0 \times 10^1$ = lower limit of the assay.

From the foregoing test results and from known dosage ranges of the "conazole compound" (14α-methyl demethylase inhibitor) and the "mevinolinic acid compound" (HMG-Co-reductase inhibitor) as applied to man, it is determined that generally from about 2.85 to about 4.75 mg/kg of body weight of the conazole compound and about 2.85 to about 4.75 mg/kg of body weight of the mevinolinic acid compound is to be employed while considering patient's health, weight, age and other factors which influence response to a drug as well as the particular drug to be employed. These amounts when expressed as doses suitable for man in the range of from about 200 to about 400 mg of each active ingredient given BID by oral or parenteral route.

According to the present invention, the synergistic antifungal or fungicidal composition may be formulated for injection and may be presented in unit dosage form in ampoules or in multidose containers, if necessary with an added preservative. The compositions may also take such forms as suspensions, solutions or emulsions in oily or aqueous vehicles, and may contain formulating agents such as suspending, stabilizing and/or dispersing agents. Alternatively, the active ingredients may be in powder form for reconstituting with a suitable vehicle prior to parenteral or oral administration.

The compounds also may be prepared in tablet or capsule form as well as in liquid form for oral administration. These also may be in unit dosage form.

For parenteral applications the drugs may be formulated in conventional parenteral solutions such as 0.85 percent sodium chloride or 5 percent dextrose in water, or other pharmaceutically acceptable compositions.

The outstanding properties are most effectively utilized when the conazole compound and the mevinolinic acid compound are formulated into novel pharmaceutical compositions with a pharmaceutically acceptable carrier according to conventional pharmaceutical compounding techniques.

In preparing the compositions in oral dosage form, the component drugs are intimately admixed with any of the usual pharmaceutical media, including for liquid preparations, liquid carriers such as water, glycols, oils, alcohols, and the like, and for solid preparations such as capsules and tablets, solid carriers such as starches, sugars, kaolin, ethyl cellulose, generally with lubricant such as calcium stearate, together with binders, disintegrating agents and the like. Because of their ease in administration, tablets and capsules represent the most advantageous oral dosage form. It is especially advantageous to formulate the compositions in unit dosage form for ease of administration and uniformity of dosage. Compositions in unit dosage form constitutes an aspect of the present invention.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured units in ampoules or in multidose containers and the like. A unit dosage of the present invention will generally contain from 200 to 400 milligrams of each of the component drugs.

The following examples illustrate novel compositions useful in the practice of the present invention, but are not to be construed as limiting:

EXAMPLE I 1000 compressed tablets containing 200 milligrams of ketoconazole and 300 milligrams of ammonium mevinolinate are prepared from the following formulation:

|  | Grams |
|---|---|
| Ketoconazole | 200 |
| Ammonium mevinolinate | 300 |
| Starch | 750 |
| Dibasic calcium phosphate hydrous | 5000 |
| Calcium stearate | 2.5 |

The finely powdered ingredients are mixed well and granulated with 10 percent starch paste. The granulation is dried and compressed into tablets.

EXAMPLE II 1000 hard gelatin capsules, each containing 210 milligrams of ketoconazole and 290 milligrams of ammonium mevinolinate are prepared from the following formulation:

|  | Grams |
|---|---|
| Ketoconazole | 210 |
| Ammonium mevinolinate | 290 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE III 250 milliliters of an injectable solution are prepared by conventional procedures having the following formulation:

| Dextrose | 12.5 grams |
|---|---|
| Water | 250 milliliters |
| Ketoconazole | 200 milligrams |
| Ammonium mevinolinate | 200 milligrams |

The ingredients are blended and thereafter sterilized for use.

Additional suitable treating compositions may be prepared by substituting a suitable amount of sodium or potassium salt of mevinolinic acid for the ammonium salt.

What is claimed is:

1. A fungicidal composition suitable for treating mycotic infections comprising a fungicidal amount in combination of:
   (1) from 200 to 400 milligrams of a compound having 14α-methyldemethylase inhibitor activity and which is named cis-1-acetyl-4-[4-[[2-(2,4-dichlorophenyl-2-(1H-imidazol e-1-yllmethyl)-1,3-dioxolan-4-yl]methoxy]phenyl]-piperazine(-ketoconazole), and
   (b 2) from 200 to 400 milligrams of a compound having HmG-CoA reductase inhibitor activity and which is a water-soluble salt of mevinolinic acid in admixture with a pharmaceutically effective carrier.

2. A composition according to claim 1 wherein the water-soluble salt of mevinolinic acid is the ammonium salt.

3. A composition according to claim 1 which is an oral composition.

4. A composition according to claim 1 which is a parenteral composition.

5. A method for killing fungi causing mycotic infections comprising administering to the site infected with fungi, a fungicidally effective amount of a composition comprising:
   (1) a compound having 14α-methyldemethylase inhibitor activity and named cis-1-acetyl-4-[4-[[2-(2,4-dichlorophenyl)-2-(1H-imidazole-1-ylmethyl)-1,3-dioxolan-4-yl]methoxy]phenyl]piperazine (ketoconazole) in an amount of from 2.85 to 4.75 mg/kg of body weight and
   (2) a compound having HmG-CoA reductase inhibitor activity and is a water-soluble salt of 7-[1,2,6,7,8,8a(R) hexahydro-2(S),6(R)-dimethyl-8(S)-(2(S)-methylbutyryloxy) naphthyl-1(S)]-3(R),5(R)dihydroxyheptanoic acid (mevinolinic acid) in an amount of from 2.85 to 4.75 mg/kg of body weight.

6. A method for treating mycotic infections comprising directing to the site where control is desired, a fungicidally effective amount of:
   (1) a compound having 14α-methyldemethylase inhibitor activity and named cis-1-acetyl-4-[4-[[2-(2,4-dichlorophpenyl)2-(1H-imidazole-1ylmethyl)-1,3-dioxolan-4-yl]methoxy]phenyl]piperazine (ketoconazole) in an amount of from about 2.85 to 4.75 mg/kg of body weight and (2) a compound having HmG-CoA reductase inhibitor activity and is a water soluble salt of 7-[1,2,6,7,8,8a(R)-hexahydro-2(S),6(R)-dimethyl-8(S)-(2(S)-methylbutyryloxy)naphthyl-1(S)]-3(R),5(R)-dihydroxyheptanoic acid (mevinolinic acid) in an amount of from about 2.85 to 4.75 mg/kg of body weight.

7. A method according to claim 6 wherein the water-soluble salt is ammonium mevinolinate.

8. A method according to claim 6 wherein the treatment is by parenteral administration.

9. A method according to claim 6 wherein the treatment is by oral administration.

* * * * *

UNITED STATES PATENT AND TRADEMARK OFFICE
CERTIFICATE OF CORRECTION

PATENT NO. : 4,871,741

DATED : Oct. 3, 1989

INVENTOR(S) : Hans H. Gadebusch/Mary E. Valiant

It is certified that error appears in the above-identified patent and that said Letters Patent is hereby corrected as shown below:

<u>In the Claims</u>:

Col. 10, line 29, change "dichlorophenyl-2-(1H-imidazol e-1-ylmethyl)-1,3-" to -- dichlorophenyl-2-(1H-imidazole-1-ylmethyl)-1,3- --

Col. 10, line 30, change "dioxolan-4-yl]methoxy]phenyl]-piperazine(-" to -- dioxolan-4-yl]methoxy]phenyl]-piperazine --

Col. 10, line 31, change "ketoconazole), and" to -- (ketoconazole), and --

Col. 10, line 32, change "(b 2) from 200 to 400 milligrams of a compound hav-" to -- (2) from 200 to 400 milligrams of a compound hav- --

Col. 10, line 55, change "[1,2,6,7,8,8a(R)   hexahydro-2(S),6(R)-dimethyl-" to -- [1,2,6,7,8,8a(R)-hexahydro-2(S),6(R)-dimethyl- --

Col. 10, line 56, change "8(S)-(2(S)-methylbutyryloxy)   naphthyl-1(S)]-" to -- 8(S)-(2(S)-methylbutyryloxy)naphthyl-1(S)]- --

Col. 10, line 57, change "3(R),5(R)dihydroxypheptanoic acid (mevinolinic" to -- 3(R),5(R)-dihydroxyheptanoic acid (mevinolinic --

UNITED STATES PATENT AND TRADEMARK OFFICE
CERTIFICATE OF CORRECTION

PATENT NO. : 4,871,741

DATED : Oct. 3, 1989

INVENTOR(S) : Hans H. Gadebusch and Mary E. Valiant

It is certified that error appears in the above-identified patent and that said Letters Patent is hereby corrected as shown below:

Col. 10, line 65, change "(2,4-dichlorophpenyl)2-(1H-imidazole-1ylmethyl)-" to -- (2,4-dichlorophenyl)2-(1H-imidazole-1-ylmethyl)- --

Signed and Sealed this

Nineteenth Day of February, 1991

*Attest:*

HARRY F. MANBECK, JR.

*Attesting Officer*     *Commissioner of Patents and Trademarks*